(12) United States Patent
Thieberger et al.

(10) Patent No.: US 8,768,489 B2
(45) Date of Patent: *Jul. 1, 2014

(54) DETECTING AND USING HEART RATE TRAINING ZONE

(76) Inventors: Gil Thieberger, Kiryat Tivon (IL); Ari Keren-Yaar, Kiryat Tivon (IL); Tal Thieberger, Kiryat Tivon (IL)

( * ) Notice: Subject to any disclaimer, the term of this patent is extended or adjusted under 35 U.S.C. 154(b) by 1385 days.

This patent is subject to a terminal disclaimer.

(21) Appl. No.: 12/484,183

(22) Filed: Jun. 13, 2009

(65) Prior Publication Data

US 2009/0312658 A1    Dec. 17, 2009

Related U.S. Application Data

(60) Provisional application No. 61/061,504, filed on Jun. 13, 2008.

(51) Int. Cl.
*A61N 1/00* (2006.01)
*A63B 24/00* (2006.01)
*A63B 71/06* (2006.01)

(52) U.S. Cl.
CPC . *A63B 71/06* (2013.01); *A61N 1/00* (2013.01); *A63B 24/0087* (2013.01); *A63B 2230/06* (2013.01); *A63B 2220/10* (2013.01); *A63B 2220/72* (2013.01); *A63B 2230/40* (2013.01); *A63B 2230/00* (2013.01); *A63B 2220/803* (2013.01); *A63B 24/0062* (2013.01); *A63B 2071/068* (2013.01)
USPC ........................................................ 607/122

(58) Field of Classification Search
CPC ........... A61N 1/00; A61N 1/025; A61B 5/00; A61B 5/02; A61B 5/0002; A61B 5/03; A61B 5/04; A61B 5/103; A61B 5/12; A61B 5/22

See application file for complete search history.

(56) References Cited

U.S. PATENT DOCUMENTS

| | | | |
|---|---|---|---|
| 5,853,005 A * | 12/1998 | Scanlon | 600/459 |
| 7,097,588 B2 | 8/2006 | Watterson | |
| 7,486,798 B2 | 2/2009 | Anjanappa | |
| 2005/0250458 A1* | 11/2005 | Graham et al. | 455/121 |
| 2006/0169125 A1 | 8/2006 | Ashkenazi | |
| 2007/0060446 A1 | 3/2007 | Asukai | |
| 2008/0033311 A1 | 2/2008 | Sledge | |
| 2008/0045805 A1* | 2/2008 | Sarel et al. | 600/300 |
| 2008/0177157 A1* | 7/2008 | Pasricha et al. | 600/301 |

* cited by examiner

*Primary Examiner* — Eric D. Bertram
*Assistant Examiner* — Elizabeth K So

(57) ABSTRACT

Methods and devices for comprising: obtaining an estimated heart rate training zone for a user; measuring the pulse rate of the user; and performing a plurality of computerized talk tests, such that a higher number of computerized talk tests are performed when the measured pulse rate is more in the vicinity of the estimated heart rate training zone than outside the vicinity of the estimated heart rate training zone. Other embodiments include devices for controlling an exercise program, comprising: an interface to an element configured to play auditory signals, and an interface to an element configured to record a user's speech in accordance with the auditory signals; wherein the device is configured to provide an indication upon identifying involuntary interruptions in the user's speech.

18 Claims, 10 Drawing Sheets

What Target Heart Rate Will You Set In Your Polar Watch?!

- Heart rate max options
  - HRmax = 220 − age
  - HRmax = 205.8 − (0.685 * age)
  - HRmax = 206.3 − (0.711 × age)
- Target heart rate options:
  - THR = ((HRmax − HRrest) × %Intensity) + HRrest
  - THR = HRmax − Adjuster ± 5 bpm
- *And there are many more options...*

FIG. 8A

What Target Heart Rate Will You Set In Your Polar Watch?!

- And how will you compensate the Intensity/Adjuster factor for:
  - Caffeine
  - No sleep
  - Overtraining
  - Nervousness
  - Bad feeling
  - Depression
  - *And there are many more...*

FIG. 8B

'eTalk' - World's 1st Computerized Talk Test

- eTalk is the *only* talk test solution for a group of trainees (aerobics class, spinning, jogging, walking and many more...)
- With eTalk everyone can have an accurate daily personalized fitness program
- eTalk develops physical awareness and prevents sport injuries
- Simple user interface
- Easy to operate

FIG. 9 eTalk In-The-Ear

- An in-the-ear device including:
  - A speaker for playing a theme to be repeated by the trainee
  - A microphone to record the trainee's voice while repeating the theme
  - A processor for identifying involuntary interruptions (hyperpnea)
  - Optional interface with a pulse watch

FIG. 10A eTalk Throat

- A wearable device including:
  - A throat microphone to record the trainee's voice while repeating the theme
  - A processor for identifying involuntary interruptions (hyperpnea)
  - Optional interface with a pulse watch
- A speaker for playing a theme to be repeated by the trainee
  - Loudspeaker for the entire group *OR* earphone for each trainee

FIG. 10B eTalk Cellphone

- An ordinary cellphone:
  - Calling the eTalk service
  - Service computer plays a theme to be repeated by the trainee
  - Cellphone records the trainee's voice while repeating the theme
    - optional throat microphone
- The eTalk service:
  - identifies involuntary interruptions (hyperpnea) through the cellphone call, and then
  - indicates to the user to read his pulse watch

FIG. 10C

US Health Clubs

- Over 40,000,000 U.S. health club members
- 30% yearly attrition rate in for-profit health clubs
- Pain – high quality personalized training is expensive
- Gain – eTalk provides simple inexpensive personalized training programs for spinning, aerobics classes, treadmill and rowing

FIG. 11A

Pregnancy

- 4,000,000 live births in the U.S. each year
- Pain:
  - Overtraining is dangerous (fetal distress, IUGR, and maternal injuries)
  - No training results in significant weight gain;
  - thin physique with no training is susceptible to increased mineral drain resulting in anemia, bone loss and weakening teeth
- Gain:
  - eTalk sets target heart rate safety zone to prevent overtraining
  - Given the average tendency to undertrain, eTalk encourages safe harder training

FIG. 11B

US Armed Forces

- Almost 200,000 new recruits join active duty every year
- 37,000 marines undergo central training every year
- Pain - Training out of the target heart rate range results in a slower progress and disruptive injuries
- Gain – eTalk provides the optimal physical training program and reduces injuries

FIG. 11C

DETECTING AND USING HEART RATE TRAINING ZONE

CROSS-REFERENCE TO RELATED APPLICATIONS

This application claims the benefit of U.S. Provisional Patent Application No. 61/061,504, filed Jun. 13, 2008.

BACKGROUND

Some trainees rely on target heart rate, determined in an all-out exercise test performed once a season, for setting their training program. Other trainees rely on estimated target heart rate, usually based on a prediction formula or a coach's assessment, for setting their training program.

However, it is not uncommon during certain days to begin an aerobic practice feeling terrific, only to be limited by a pulse tracking device which doesn't stop beeping when that activity is sustained beyond the comfort zone kept in the pulse tracking device. Alternatively, it is not uncommon during certain days to have a 'bad day' in which it is too strenuous to practice within the comfort zone kept in the pulse tracking device.

At sub-ventilatory threshold activity levels, when energy consumption and ventilation are less than at the ventilatory threshold, the user's aerobic metabolism sustains physical effort for the most part. Such activity levels can therefore be sustained for extended periods of time. For example, long distance runners aim for such activity levels for most of a marathon. At supra ventilatory threshold activity levels, when energy consumption and ventilation are greater than at the ventilatory threshold, the user's aerobic metabolism is complemented by anaerobic metabolism to a degree that will cause cessation of exercise before long, most probably due to accumulation of anaerobic metabolism by-products. It is to be noted that for most clinical and practical purposes, the ventilatory threshold is equated here with the anaerobic threshold, which, for the same purposes, is on a par with the blood lactate threshold.

When a patient is in the recovery stage from a heart or lung disease, especially in the case of rehabilitation using a training device, training itself could be dangerous for the patient if it is carried out without correctly assessing the variations in his/her physical conditions, which occur from time to time.

The talk test is a well-known method for assessing the current heart rate training zone that corresponds to the user's ventilatory threshold. One talk test example includes the following stages:

In the first stages of exercise, the user can breathe deeply in a timely manner, accommodating both the fluency of his/her conversation and the increasing needs of respiration.

In a further stage, as pace is maintained, and the user resumes talking towards the end of the stage, it may become apparent to the human ear that a few long sentences (such as over 10 words, or linked sentences with more than one clause) are interspersed with shorter sentences. A user may further modify his/her diction, or choice of words, for example by first expressing his/her feeling in "yes, as you can see I am doing quite nicely", to be followed by the more condensed form of speech "you see?! I'm fine!". Alternatively, a user may be prone to squeezing out the last words in every sentence, varying his/her pitch, as well as uttering words more quickly.

Inhalations change in quality as the test progresses. In between sentences uttered, or lines of a song or recited paragraph, or hummed tunes of a musical piece, inhalations become deeper as a manifestation of hyperpnea.

A consistent observation made during this further stage, usually used to infer exceeding the "ventilatory threshold zone", is of interruptions constituting, in addition to deeper inhalations in between sentences, pauses in the middle of some sentences. If during these interruptions a labored pattern of inhalation takes place, then the ventilatory threshold has been reached or exceeded.

Continuing the test may serve as validation. As effort continues to increase, interruptions in even short sentences or recitation pieces become regular and unavoidable. However, this stage is most often interpreted as exceeding the bounds corresponding to the ventilatory threshold.

Optionally, the ventilatory threshold is reached when the voice produced by the user whether singing, whistling, or humming, begins to break down into pauses (for inspiration) which are discordant with the breaks or softer notes in the melody. Alternatively or additionally, the ventilatory threshold is reached when the user's voice significantly changes its pattern.

In some cases, the talk test is performed with a psychophysiological scale, such as the Rate of Perceived Exertion (RPE) test. The level of perceived exertion may be assessed with almost any category scale such as:

A) The Borg scale that includes the rates: 6—No exertion at all, 7—Extremely light exertion, 8, 9—Very light exertion, 10, 11—Light exertion, 12, 13—Somewhat hard, 14, 15—Hard (heavy), 16, 17, 18, 19—Extremely hard, and 20—Maximal exertion.

B) An RPE scale that includes: Moderate Zone: RPE 4-5 (approximately 50% of maximum heart rate); RPE 6-7 (approximately 60-70% of maximum heart rate); RPE 7-8 (approximately 70-80% of maximum heart rate); and RPE 8-10 (approximately 80-100% of maximum heart rate).

C) An RPE scale that includes: 1—No exertion at all, 2—Very light exertion, 3—Light exertion, 4, 5—Somewhat hard, 6, 7—Hard (heavy), 8, 8.5—Very hard, 9, 9.5—Extremely hard, and 10—Maximal exertion.

In some cases, training programs are based on one or more of the following parameters: target heart rate, heart rate training zone, anaerobic threshold, ventilatory threshold, intensity factor, adjuster factor, or the maximum estimated target heart rate. However, these parameters may be influenced by environmental conditions, the user's physiological condition, and/or the user's psychological condition. FIG. 8A and FIG. 8B illustrate some problems related to setting the target heart rate.

BRIEF SUMMARY

In one embodiment, a method comprising: obtaining an estimated heart rate training zone for a user; measuring the pulse rate of the user; and performing a plurality of computerized talk tests, such that a higher number of computerized talk tests are performed when the measured pulse rate is more in the vicinity of the estimated heart rate training zone than outside the vicinity of the estimated heart rate training zone. Optionally the method further comprising performing at least one of the computerized talk tests while the user sustains a fixed level of effort. Optionally the method further comprising obtaining from a controllable exercise device an indication that the user is sustaining the fixed level of effort. Optionally the method further comprising an effort-assessment-device based on which it is determined that the user approximately sustains the fixed level of physical effort. Optionally the method further comprising determining that the user approximately sustains the fixed level of physical effort by receiving successive RPE indications within a predetermined close range. Optionally, the estimated heart rate training zone is received from the user. Optionally, the estimated heart rate training zone is the user's last target heart rate. Optionally, the estimated heart rate training zone is calculated using data about the user. Optionally, the data about the user comprises one or more of the following: age, sex, height, weight, chest size, blood pressure, activity level, training history, exercise objectives, mental condition, motivation level, body temperature, amount of time since last meal, resting pulse rate, hour of the day, amount of time since last long sleep, body type, and body fat measurement. Optionally, the estimated heart rate training zone is based on historic data of the user. Optionally the method further comprising identifying a change, greater than a threshold, in the user's level of effort, and implementing one or more of the following: disregarding pulse readings obtained while the level of effort changes, indicating the user to maintain the current level of effort while taking the talk test, repeating the talk test after the user sustains a level of effort, or varying the duration of the talk test.

In one embodiment, a computerized talk test device coupled to a microphone, a speaker, and a pulse meter; the computerized talk test device is configured to obtain an estimated heart rate training zone of a user, obtain pulse measurements of the user, and perform relatively more computerized talk tests when the measured pulse is more in the vicinity of the estimated heart rate training zone than outside the vicinity of the estimated heart rate training zone. Optionally, the computerized talk test device is configured to receive the estimated heart rate training zone by a voice indication through the microphone. Optionally, the computerized talk test device is further coupled to an input component, and the device receives the estimated heart rate training zone through the input component. Optionally, the computerized talk test device is further configured to perform at least one of the computerized talk tests while the user approximately sustains a fixed level of effort. Optionally, the computerized talk test device is further configured to communicate with a controllable exercise device, whereby the coordination between the computerized talk test device and the controllable exercise device enables the performance of the computerized talk test while the user approximately sustains the fixed level of effort. Optionally, the computerized talk test device is further configured to communicate with an effort-assessment-device, whereby the coordination between the computerized talk test device and the effort-assessment-device enables the performance of the computerized talk test while the user approximately sustains the fixed level of effort. Optionally, the microphone is a conduction microphone enabling operation in a noisy environment. Optionally, the computerized talk test device is an in-the-ear computerized talk test device.

In one embodiment, a device for controlling an exercise program, comprising: an interface to an element configured to play auditory signals, and an interface to an element configured to record a user's speech in accordance with the auditory signals; wherein the device is configured to provide an indication upon identifying involuntary interruptions in the user's speech. Optionally the device further comprising an interface to a controllable exercise device; wherein the controllable exercise device advances its entering into a cool-down phase based on the identification of the involuntary interruptions. Optionally the device further comprising an interface to a temperature sensor configured to measure the user's temperature; wherein the controllable exercise device advances its entering into a cool-down phase based on an indication that the user's temperature passed a temperature threshold.

In one embodiment, a method for performing a computerized talk test using a communication device, comprising: recording, using the communication device, a user's voice while training; analyzing the recordings to identify when the user reaches the ventilatory threshold and then using the communication device to instruct the user to read his/her pulse rate. Optionally, the communication device is a cellular phone. Optionally the method further comprising the step of downloading to the cellular phone software for identifying involuntary interruptions in the user's speech. Optionally the method further comprising receiving, using the cellular phone, an RPE indication from the user. Optionally the method further comprising using the cellular phone to instruct the user to read his/her pulse rate when reaching an RPE threshold.

In one embodiment, a method for performing a computerized talk test using a communication device, comprising: calling a talk test service using the communication device; performing the computerized talk test; and transmitting the user's voice to the talk test service for analysis. Optionally the method further comprising receiving an RPE indication from the user using the communication device, and determining the heart rate training zone based on the user's voice and the RPE indication. Optionally the method further comprising identifying involuntary interruptions in the user's voice. Optionally, performing the computerized talk test further comprises providing, by the talk test service, an auditory signal according to which the user should talk. Optionally the method further comprising receiving, using the communication device, an RPE indication from the user. Optionally the method further comprising determining by the talk test service when to instruct the user to read his/her pulse rate. Optionally the method further comprising obtaining the user's pulse rate from a pulse meter by the communication device using short range communication, and forwarding the obtained pulse rate to the talk test service. Optionally the method further comprising the step of determining, by the talk test service, approximately when the user will speak for the purpose of the talk test.

In one embodiment, a method for assessing a training zone of a heavy-load exercise, comprising: performing at least one computerized talk test and at least one RPE test while the user trains with load similar to the load in the expected heavy-load exercise. Optionally the method further comprising performing the computerized talk test while the user approximately sustains a fixed level of effort. Optionally the method further comprising assessing the level of effort using an effort-assessment-device. Optionally, the computerized talk test is performed while the user undergoes the heavy-load exercise. Optionally, the user is dressed in the gear she/he is expected to wear in the heavy-load exercise. Optionally, the computerized talk test is performed using an in-the-ear device. Optionally, the computerized talk test is performed using a throat microphone.

Implementations of the disclosed embodiments involve performing or completing selected tasks or steps manually, semi-automatically, fully automatically, and/or a combination thereof. Moreover, depending upon actual instrumentation and/or equipment used for implementing the disclosed embodiments, several embodiments could be achieved by hardware, by software, by firmware, or a combination thereof. In particular, with hardware, embodiments of the invention could exist by variations in the physical structure. Additionally, or alternatively, with software, selected functions of the invention could be performed by a data processor, such as a computing platform, executing software instructions or protocols using any suitable computer operating system.

BRIEF DESCRIPTION OF THE DRAWINGS

The embodiments are herein described, by way of example only, with reference to the accompanying drawings. No attempt is made to show structural details of the embodiments in more detail than is necessary for a fundamental understanding of the embodiments. In the drawings:

FIG. 8A and FIG. 8B illustrate some problems related to setting the target heart rate;

FIG. 9 illustrates some non-limiting benefits of some of the disclosed embodiments;

FIG. 10A illustrates one non-limiting example of an in-the-ear device;

FIG. 10B illustrates one non-limiting example of a device including a throat microphone;

FIG. 10C illustrates one non-limiting example of a device based on a cellular phone; and FIG. 11A, FIG. 11B, and FIG. 11C illustrate some non-limiting uses for some of the disclosed embodiments.

DETAILED DESCRIPTION

Figure 1:
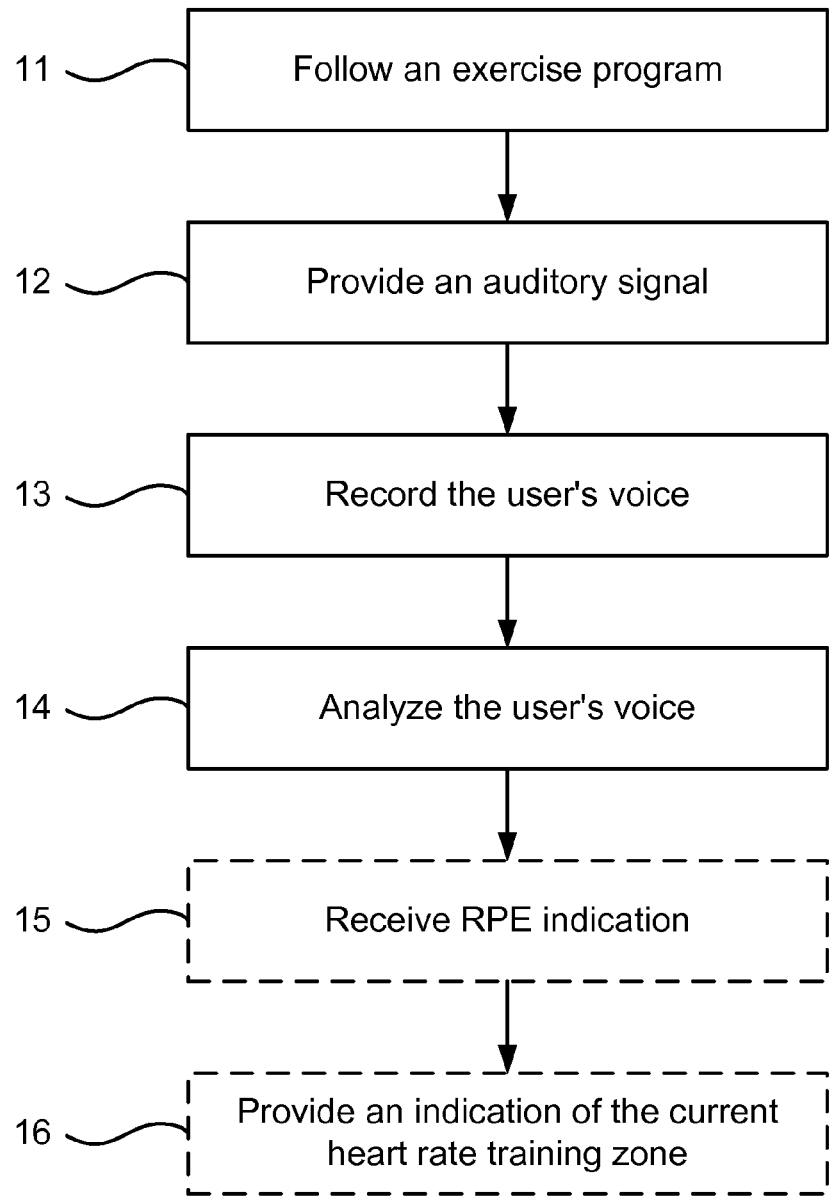
FIG. 1 illustrates one embodiment of a computerized talk test.

In the following description, numerous specific details are set forth. However, the embodiments of the invention may be practiced without some of these specific details. In other instances, well-known hardware, software, materials, structures and techniques have not been shown in detail in order not to obscure the understanding of this description. In this description, references to "one embodiment" or "some embodiments" mean that the feature being referred to may be included in at least one embodiment of the invention. Moreover, separate references to "one embodiment" or "some embodiments" in this description do not necessarily refer to the same embodiment. Illustrated embodiments are not mutually exclusive, unless so stated and except as will be readily apparent to those of ordinary skill in the art. Thus, the invention may include any variety of combinations and/or integrations of the features of the embodiments described herein. Also herein, flow diagrams illustrate non-limiting embodiment examples of the methods, and block diagrams illustrate non-limiting embodiment examples of the devices. Some operations in the flow diagrams may be described with reference to the embodiments illustrated by the block diagrams. However, the methods of the flow diagrams could be performed by embodiments of the invention other than those discussed with reference to the block diagrams, and embodiments discussed with reference to the block diagrams could perform operations different from those discussed with reference to the flow diagrams. Moreover, although the flow diagrams may depict serial operations, certain embodiments could perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. Furthermore, methods and mechanisms of the embodiments will sometimes be described in singular form for clarity. However, it should be noted that some embodiments may include multiple iterations of a method or multiple instantiations of a mechanism unless noted otherwise. For example, when a controller or an interface are disclosed in an embodiment, the scope of the embodiment is intended to also cover the use of multiple controllers or interfaces.

The Computerized Talk Test

FIG. 1 illustrates one embodiment of a computerized talk test. In step 11, the user follows a predefined exercise program. In step 12, the user is provided with auditory signals from time to time. In step 13, recording of user talking according to the auditory signals; for example, the user may accompany or repeat the auditory signal in his/her voice. In step 14, analyzing the recording for predefined properties, such as involuntary interruptions in the user's voice and/or other patterns and characteristics appropriate to the talk test. Optionally, the computerized talk test is coordinated with a pulse meter. In optional step 15, receiving RPE indication from the user. Optionally, each time a talk test is performed the user's pulse rate is measured and may be stored in the device. And in optional step 16, providing an indication of the user's current heart rate training zone based on the analysis results. The indication may be a pulse rate value matching the user's current heart rate training zone.

It is noted that most of the embodiments discussed may be implemented either with a pulse meter or with a heart rate monitor/meter. For purpose of clarity, the terms "pulse rate" and "pulse meter" are mostly used herein, and it is to be understood that in many embodiments they may be replaced by "heart rate" and/or almost any type of heart rate monitor/meter. Moreover, for purpose of clarity, the terms "heart rate training zone" and "target heart rate" are mostly used herein, and it is to be understood that in many embodiments they may be replaced with alternative terms, such as, but not limited to, "pulse rate training zone", and "target pulse rate".

Referring to step 11, one example of the predefined exercise program includes one or more stages, each stage including: (i) continuous aerobic activity for about 1 to 4 minutes, (ii) talking for about 15 to 120 seconds, and, optionally, (iii) providing an RPE indication. In one embodiment, each consecutive stage features higher aerobic activity intensity than its antecedent stage. Optionally, the predefined exercise program stops when talking is difficult and/or the RPE is rated 'somewhat hard' or 'hard', and/or pulse rate has reached a predefined limit, or the user requests termination of the test.

One talk test example, in which a treadmill is used to set a target heart rate for running, may begin with a 3 minute warm up at the user's usual walking speed (for example about 5 km/hr); continue with increased speed (for example about 6.5 km/hr); then, after 2 minutes, the user is cued to talk (for analysis of the speech), is optionally requested to provide his/her RPE indication, and the pulse rate is recorded; this is continued by raising the speed, for example, to 6, 7, 8, 9, and 10 km/hr, where for each increase in the speed, after about 2 minutes, the user is cued to talk, requested to provide RPE indication, and the pulse rate is recorded. Similar tests may be performed on a stationary bike, step machine, rowing machine or any other machine that controls the velocity and/or effort of the user. Similar tests may be performed without a machine that controls the velocity and/or effort, but by a trainer who sets the pace, and/or by the trainee himself who increases the pace gradually. Optionally, sensors and measurements, such as disclosed in US patent application number 20070060446, entitled: "Sound-output-control device, sound-output-control method, and sound-output-control program", incorporated herein by reference in its entirety, are utilized for the exercise program.

Referring to step 12, examples of accompaniment of the auditory signal may include singing, talking, reciting, humming, or whistling. Auditory signal examples include, but are not limited to, word(s), sentence(s), song(s), or melodi(es). Optionally, the auditory signal is predetermined, for example, the user recites a predefined musical piece, theme, song, or a literary piece. Using a predefined auditory signal may assist the device in analyzing the user's voice. For example, the user may record a recited piece and repeat that recited piece each time a talk test is taken. In this case, the device compares its stored recited piece with the current performance of the user. Alternatively, the device includes voice analysis capabilities enabling it to identify involuntary interruptions, as discussed below.

Alternatively, the user is not provided with an auditory signal while taking the computerized talk test. In this case, the user has to decide what to say every so often, which may disturb some users because of the mental effort required to plan the sentences uttered.

Referring to step 13, almost any kind of microphone 25 and sampling hardware (that may be implemented by the processor 22 and memory 21) may be utilized for recording the user's voice. The microphone may be integrated with the computerized talk test device or coupled to it. The microphone may be attached to the user by any appropriate means.

Referring to step 14, for identifying the involuntary interruptions in the user's voice, perhaps resulting from hyperpnea, one or more of the disclosed embodiments may utilize many known voice analysis methods, audio signal processing methods, speech processing methods, speech recognition methods, or other digital or analog signal processing methods. The involuntary interruption identification may be fully automatic, semi automatic or performed by a human operator.

In some embodiments, the involuntary interruptions in the user's voice may be detected based on using one or more of the following methods: analysis of sound phase changes, noise contribution, noise power, signals overlapping, comparison and/or analysis of acoustic models, recognition of sound patterns, and/or frequency response analysis.

In some embodiments, there is no need to perform speech recognition because it is sufficient in many cases to identify involuntary interruption sounds, which include hyperpnea sounds, to determine that the user has reached the ventilatory threshold, and/or the anaerobic threshold. For example, the device may use the pitch, frequency, loudness, entropy, and/or any other appropriate predefined characteristic of the user's voice to recognize when the user reaches the ventilatory threshold.

For example, based on the auditory signal (optionally produced by the computerized talk test device, which guides the user), the device may be able to estimate the expected pitch of the user's voice at specific times, and/or the expected relations between specific pitches at specific times. The device may then recognize when the user reaches the ventilatory threshold and/or when involuntary interruptions occur, by observing when the pitch of the user's voice does not conform to the estimated pitch and/or to the estimated pitch relations.

As another example, based on the auditory signal, the device may be able to estimate the frequency of the user's voice. In this case, the device observes the frequency of the user's voice. When the user reaches the ventilatory threshold and/or when involuntary interruptions occur, the frequency of the user's voice does not conform to the estimated frequency.

As another example, based on the auditory signal and/or based on prior recordings by the user, the device may be able to estimate the loudness and/or intensity of the user's voice. In this case, the device observes the loudness and/or intensity of the user's voice. When the user reaches the ventilatory threshold and/or when involuntary interruptions occur, the characteristics of the loudness of the user's voice change. The loudness may be estimated based on sound pressure and/or spectrum of the harmonics and the physical duration of the analyzed voice.

As another example, when the user repeats the same text, the device may compare the entropy of one or more of the former recordings by the user with the entropy of one or more of the later recordings by the user. When the user reaches the ventilatory threshold and/or when involuntary interruptions occur, the entropies of the later and former recordings may have different values. For example, a pregnant woman may begin the test with a baseline including some hyperpnea and a higher pulse rate than her baseline before her pregnancy.

In one embodiment, the device filters the user's voice and analyzes only a predefined set of frequencies and/or harmonics. In one embodiment, the device smoothes the recorded voice before analyzing it. In one embodiment, the device transforms the recorded voice to a predefined domain and/or to a predefined frequency, and then optionally filters the recorded voice, and analyzes its characteristics.

Referring to step 15, in one embodiment, a healthy exerciser should feel as if he is working "somewhat hard" to "hard" according to the RPE scale during an aerobic exercise or training session. The device may inquire about the RPE level from time to time. The RPE indication may be received though any appropriate means, such as voice indication, pressing a button, touching an electronic element, setting a switch, or using an electro-optics detector. In one embodiment, the RPE and the talk test are complementary tests. Depending on their physical state, including but not limited to hydration status, remaining strength, fatigue or discomfort of muscles or other parts of the body, users may indicate through the RPE that they prefer not to complete the test and/or to alter the results of the computerized talk test.

In one embodiment, a personalized RPE scale may be programmed into the control software. Optionally, the software may have an algorithm for the user to plug in individual personal data and/or to personalize the RPE scale. Personalizing the RPE scale may enable one to synchronize one's mind with one's body more thoroughly through the computerized talk test and one's own feelings.

Referring to step 16, the indication of the user's current heart rate training zone may include explicit value(s), especially when the computerized talk test device has access to pulse measurements; may include a notification to the user to read the pulse rate from a meter by himself/herself, may include a notification to the user to measure the pulse rate; and/or other alternatives which enable the user to assess the current heart rate training zone.

Hardware Elements

Figure 2:
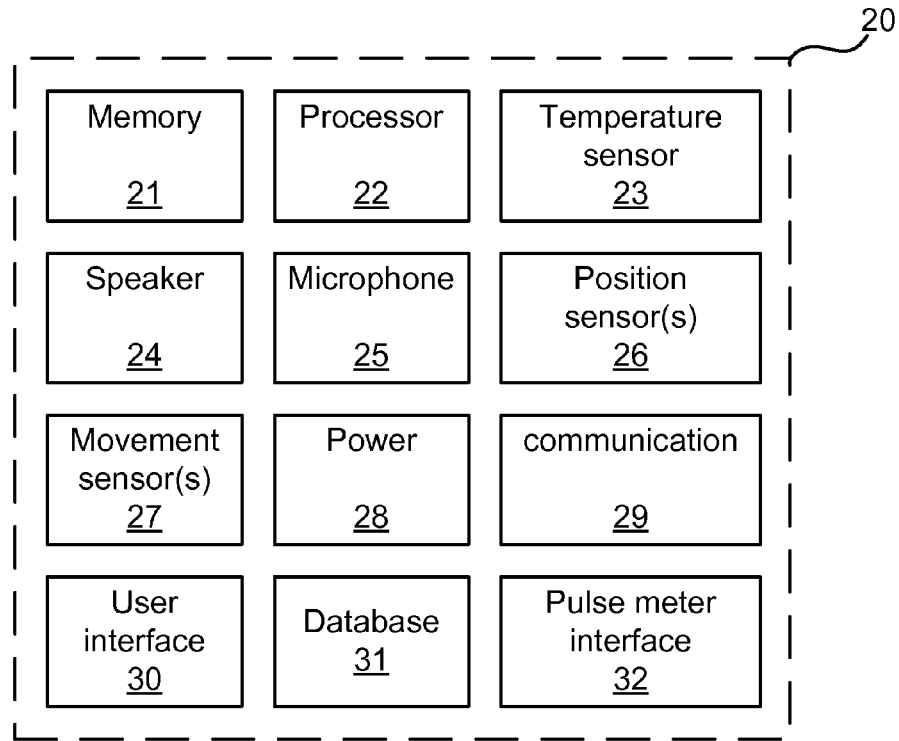
FIG. 2 illustrates some hardware elements that may be utilized for some of the embodiments of the computerized talk test device.

FIG. 2 illustrates some hardware elements that may be utilized for some of the embodiments of the computerized talk test device 20. It is to be understood that many embodiments may include only a few of the hardware elements illustrated in FIG. 2. Additional hardware elements may be added as needed.

Figure 3:
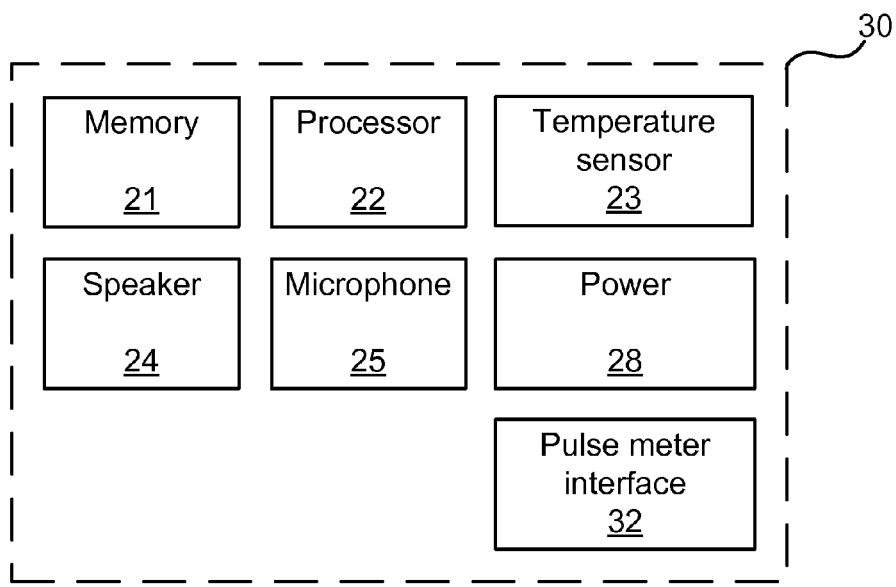
FIG. 3 illustrates one embodiment of hardware elements useful for an in-the-ear computerized talk test device.

FIG. 3 illustrates one embodiment of hardware elements useful for an in-the-ear computerized talk test device. In one embodiment, the in-the-ear computerized talk test device does not include the temperature sensor 23 and the pulse measuring interface 32. The power source 28 may be located inside the in-the-ear device. Alternatively, the power source may be located outside the ear, and in that case, power element 28 represents an interface to the power source.

In one embodiment, the temperature sensor 23 is used for measuring the trainee's body temperature, which may be useful for preventing heat-related problems. In one embodiment, the device is used by a pregnant woman and an optional alarm is operated when the woman's body temperature rises by 1.5 degrees Celsius over baseline, or anytime core temperature reaches 38.5 degrees Celsius. In one embodiment, the device includes a predefined temperature threshold, and an optional indication is initiated when the user's temperature passes the threshold. Additionally or alternatively, the device communicates with a controllable exercise device that enters a cool-down phase when the user's temperature passes the threshold temperature. Additionally or alternatively, the device communicates with a controllable exercise device that advances its entering into a cool-down phase based on an indication that the user's temperature has passed a temperature threshold.

In one embodiment, the one or more position sensors 26 measure the angular position of the user's body. In one example, the user is a pregnant woman and a position sensor is utilized for detecting whether the woman is lying on her back. Optionally, after a predefined duration of time in which it is estimated that the pregnant woman is lying on her back, an appropriate indication is initiated; the indication may include a voice message saying it is unhealthy for a pregnant woman to lie on her back. In another example, one or more movement sensors 27 may indicate when the pregnant woman is bouncing excessively, since this activity is not recommended during pregnancy. Moreover, the movement sensor 27 may indicate, for the pregnant woman, during which stage of the computerized talk test bouncing was pronounced enough to effect hyperpnea, perhaps resulting from the raised position of the thoracic diaphragm, particularly as pregnancy progresses.

In another example, the measurements of the position sensors are used to indicate to the user to improve posture, or for other medical usages.

In one embodiment, the one or more movement sensors 27 are utilized for estimating one or more of the following: (i) the distance the user attains, (ii) the work performed by the user, (iii) the exercise intensity level, (iv) the location of the user in relation to other users, (v) the movement of the user in relation to other users, or (vi) the user's alertness, vigor, or energy level.

The readings of the position sensor 26 and/or the movement sensor 27 may be utilized for better analyzing the user's voice. For example, the user's voice may be influenced by the angular position of the user's head and/or by movements performed by the user.

The computerized talk test and/or the analysis of the measurement(s) may be improved and/or simplified using a database 31. The database 31 may store data relevant to a specific user, general statistics, comparative statistics, time and date statistics, and/or any other data that may be relevant. For example, the database may be used to identify and/or assess the factors that affect performance, whether intrinsic, such as exercise type and/or frequency of exercise, environmental such as terrain and/or noise, diurnal, and/or seasonal factors.

It is to be understood that the disclosed embodiments and/or hardware elements referring to the talk test may also include or be relevant to the computerized RPE indication.

In one embodiment, the microphone 25 used to measure the user's voice for the talk test is also used for measuring breathing sounds. Alternatively, the breathing sounds are measured by another microphone and/or by other appropriate means. Optionally, the measured breathing sounds are used as a marker for assessing the exercise intensity. In one embodiment, breathing sounds, such as the breathing rate, relate to the ventilatory threshold and optionally, the target heart rate may sometimes be replaced with a target breathing rate. In one embodiment, a microphone may be used as a cough counter.

In one embodiment, the computerized talk test device 20 includes an interface 32 to a pulse meter, which may also be a heart rate meter/monitor. Herein, when a device includes an interface to something, that something can also be included in/integrated with the device; for example, because the computerized talk test device 20 includes the interface 32 to the pulse meter, the pulse meter may also be embedded in the computerized talk test device 20. The pulse rate may be measured by any pulse meter such as, but not limited to, a pulse watch, an in-the-ear device, a chest band or strap, a handrail pulse rate sensor, a handgrip pulse rate sensor, an electrocardiograph, a cardiac pacemaker, or cardiac-resynchronization-therapy device. In one embodiment, the pulse meter includes a heart-rate sensor supporting a photoelectric-pulse-wave-detection method, for example, to measure the pulse rate of the user via the earlobe while the user is exercising.

In some embodiments, some or all of the physiological signal sensors communicate wirelessly with a controller. For example, a user may wear a wireless wrist sensor to monitor or measure the pulse rate, or may wear a chest strap sensor configured to measure heart rate. Each of the sensors may be configured to communicate pulse rate signals or information to a physiological sensor interface. Additionally or alternatively, the sensors may be configured to communicate with a wireless network access point, transmitting physiological information directly to one or more servers via a network.

In one embodiment, a processor 22 or a controller is utilized for performing one or more of the following functions: operating an element of the device, such as one or more of the elements illustrated in FIG. 2; providing a user interface; managing the exercise program for the user and/or coach; and/or saving recordings. The saved recordings may be predefined, determined by a user, of predetermined episodes, or featuring predefined characteristics. The saved recordings may include, but are not limited to: user's voice recordings, various measurements of the user, various measurements of the environment, relevant statistics, actual performances, settings of the exercise machine, or data relevant for the computerized talk test.

Timing the Step of Providing the Auditory Signal

In one embodiment, the exercise program accompanying the talk test includes two or more increased effort aerobic activities. In some embodiments, because of muscular recruitment and attendant shifts in muscular energy utilization, it is preferred (for the purpose of the test) not to consider the initial stage of one or more of the increased effort aerobic activities. Therefore, the device may identify and ignore the beginning of the increased effort stages. For example, if the device plans to run a talk test on time t1, but the user has increased his/her effort shortly before time t1, the device may run the talk test sometime later on time t2. In one embodiment, the talk test is to be performed after the user sustains a fixed level of effort, which may be predetermined in some cases. Maintaining a fixed level of effort may be easy to achieve while exercising on a treadmill, a stationary bike, a step machine, a rowing machine, or another instrument that controls the velocity and/or effort (herein referred to as "controllable exercise device"), but may be more complicated without such a device or feedback.

In one embodiment, the device provides the auditory signal to begin the computerized talk test only after it receives an indication that the user approximately sustains a fixed level of effort. The indication may result from an assessment or estimation performed by the device itself and/or received from another device. A device for assessing the level of effort ("effort-assessment-device") may by based on one or more inputs from one or more of the following non-limiting sources: accelerometer; pedometer; personal navigation system, gyroscope, GPS, and/or breathing frequency meter. In one embodiment, the position sensor 26 and/or the movement sensor 27 are utilized for estimating whether the user approximately sustains a fixed level of effort. In one embodiment, the effort-assessment-device does not estimate the level of effort but is utilized to estimate whether the user approximately sustains the same level of effort; in other words, the effort-assessment-device may be utilized to estimate one or more derivatives of the level of effort. The assessment itself, based on the received readings, may be performed using many known methods for assessing physiology, movement, effort, progression, and/or energy utilization, or may be performed using new assessment methods to be conceived by a person skilled in the art, optionally after reading the teachings herein.

In one embodiment, when the readings of the effort-assessment-device are within a predefined range, or feature certain characteristics, it may be reasonable to assume that the user approximately sustains a fixed level of effort and a more accurate talk test may be carried out. Optionally, the computerized talk test device begins the talk test some time after the user has approximately sustained the particular level of effort, such that further stabilization of the exerciser's body is reached. The period of time after the user has approximately sustained the level of effort may be a predefined period of time, or may be a function of one or more parameters optionally related to the user and/or the environment.

In one embodiment, the computerized talk test device monitors the user's level of effort while taking the talk test. Whenever the computerized talk test device identifies changes in the user's level of effort—for example, a reduced or increased running rate—one or more of the following step examples may be implemented: (i) Disregarding readings obtained while the level of effort changes. (ii) indicating the user to maintain the current level of effort while taking the talk test. (iii) Repeating the talk test after the user sustains a level of effort. Or (iv) Varying the duration of the talk test. For example, if the talk test is to be disregarded and/or backed-up with additional talk tests, the talk test may be shortened. Alternatively, the talk test may be prolonged in order to increase its accuracy and/or reliability.

In one embodiment, the user is prompted every short interval, such as 30 seconds, for his/her RPE and the next stage of the talk test is issued after the RPE readings are within a predetermined close range.

In one embodiment, at least one effort-assessment-device, as described above, is used for assessing the efforts of a group of people training at a similar level of effort. For example, a group of users, proceeding approximately together, are walking or running outside. One of the users carries the effort-assessment-device, which, according to this example, measures distance, rate, and/or acceleration. When the change in distance over time is approximately constant, it may be estimated that the group of users maintains a certain level of effort. Then, each member of the group may take the computerized talk test using its own computerized talk test device 20. The plurality of computerized talk test devices carried by the group participants may be synchronized with the level of effort measuring device, and/or may communicate with the effort measurement device, and/or may communicate with a device that communicates with the effort measurement device. Without limiting the disclosed embodiments, "communication" may employ a unidirectional and/or bidirectional communication. In one embodiment, estimations from more than one effort measurement devices are combined to achieve a better assessment of the group's effort.

In one embodiment, the device automatically or manually decreases or increases the workload for the next workout. For example, if the user was unable to complete the exercise derived from the determined current heart rate training zone, the device may decrease the workload for the next workout automatically or manually, to make it less challenging for the user. The heart rate training zone may be continually reduced if the user is repeatedly unable to complete the exercise.

In one embodiment, the device provides the user with a comparison between the current target heart rate training zone and a predicted target heart rate. The predicted target heart rate may be calculated according to the Karvonen method, the Zoladz method, or any other appropriate method. Optionally, the device may fine-tune the talk test according to the predicted target heart rate. Optionally, the user may command the computerized talk test device to lead up to effort levels that bring the pulse to within the range of the predicted target heart rate.

Focusing the Device on an Estimated Heart Rate Training Zone

In one embodiment, data about the user may be stored on any kind of storage element, and/or received from the user using a user-interface. The data about the user may include, but is not limited to, one or more of the following parameters: age, sex, height, weight, chest size, blood pressure, activity level, training history, exercise objectives, mental condition, motivation level, body temperature, amount of time since last meal, resting pulse rate, hour of the day, amount of time since last long sleep, body type, body fat percentage, type and amount of additional weight carried, relevant athletic equipment, or sports gear.

The data about the user may be utilized for estimating the user's heart rate training zone. Alternatively, the user's target heart rate or estimated heart rate training zone is obtained from the user or from a third party, such as a trainer or a physician. The user's target heart rate is used for focusing the talk tests on the relevant pulse rate ranges. For example, if the user's estimated target heart rate is 130 bpm, the computerized talk test device may try to run talk tests when the user's measured pulse rate obtains the following approximate values: 105, 115, 123, 130, 137, 145, and 155. If the user's estimated target heart rate is 180 bpm, the computerized talk test device may try to run talk tests when the user's measured pulse rate obtains the following approximate values: 150, 162, 170, 176, 182, and 190.

Figure 6A:
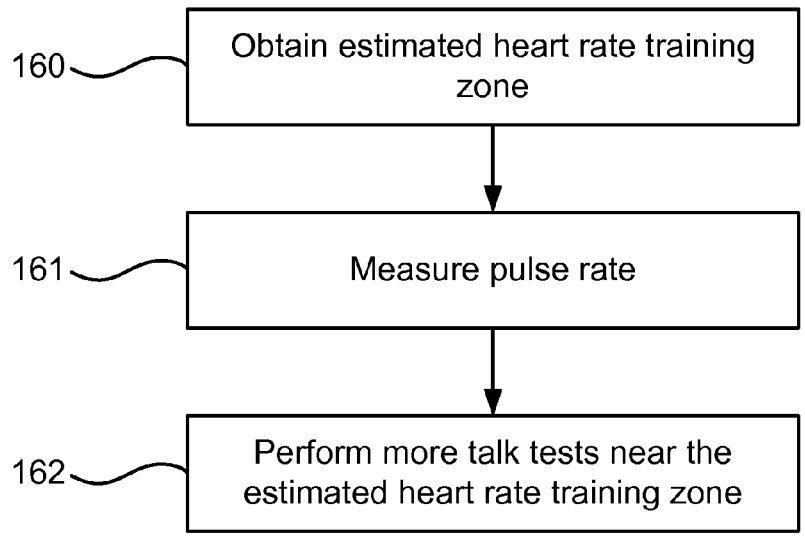
FIG. 6A illustrates one embodiment of a computerized talk test method.

FIG. 6A illustrates one embodiment of a computerized talk test method including the following steps. In step 160, obtaining an estimated heart rate training zone for a user. For example, the estimated heart rate training zone may be obtained from the user, may be the user's last target heart rate, may be calculated using data about the user, and/or based on historic data of the user. In step 161, measuring the pulse rate of the user. And In step 162, performing a plurality of computerized talk tests, such that a higher number of computerized talk tests are performed when the measured pulse rate is more in the vicinity of the estimated heart rate training zone than outside the vicinity of the estimated heart rate training zone. Optionally, at least one of the computerized talk tests is performed while the user sustains a fixed level of effort, which may be determined, for example, based on a controllable exercise device or an effort-assessment-device.

Figure 6B:
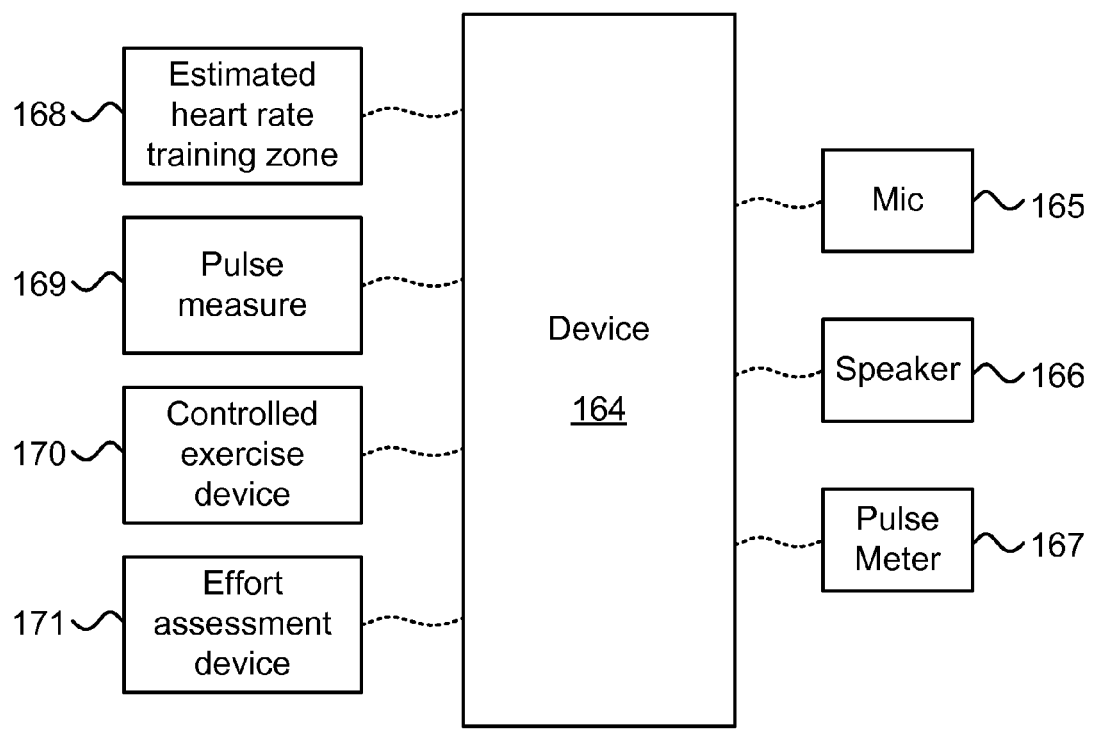
FIG. 6B is a schematic illustration of a device able to perform relatively more computerized talk tests when the measured pulse is more in the vicinity of the estimated heart rate training zone.

FIG. 6B is a schematic illustration of a device 164 able to perform relatively more computerized talk tests when the measured pulse is more in the vicinity of the estimated heart rate training zone than outside the vicinity of the estimated heart rate training zone. The device 164 includes, is coupled to, or communicates with a microphone 165, a speaker 166, and a pulse meter 167. The device 164 is configured to obtain an estimated heart rate training zone of the user 168, obtain pulse measurements of the user 169, communicate with a controllable exercise device 170, and/or communicate with an effort-assessment-device 171.

In one embodiment, a computerized talk test, optionally combined with RPE indication, is utilized for dealing with, preventing, and/or decreasing over-training and/or heavy-load problems, such as, but not limited to, stress fracture, fatigue fracture, or shin splints, all referred to herein as stress fracture. The talk test provides a reference for assessing the load applied to the user's body. The talk test may be performed on user training with a load or on user training without a load.

In one embodiment, a method for assessing a training zone of a heavy-load exercise, such as a soldier carrying heavy-load equipment, comprises performing at least one computerized talk test and RPE test while the user trains with a load similar to the load in the expected heavy-load exercise. Optionally, the user is dressed in the gear that is expected in the heavy-load exercise. Optionally, the computerized talk test is performed while undergoing the heavy-load exercise.

A significant increase or decrease in the difference between the pulse rate in the last equivocal stage and the pulse rate in the first positive stage of the talk test may indicate an over-training situation. In a normal situation, the difference between the two stages should change gradually or slowly over time. In one embodiment, a method for identifying over-training comprises: (i) running talk tests from time to time and saving the results; (ii) analyzing the changes over time of the difference between the pulse rate in the last equivocal stage and the pulse rate in the first positive stage of the talk test, and (iii) reporting an abnormal change.

In one embodiment, a highly motivated user may perceive his/her condition to be better than it actually is, and may therefore find the results of the RPE test to be inaccurate. The computerized talk test may help the highly motivated user to better conceive his/her condition by supplying an objective feedback. For example, when the highly motivated user works too hard, the computerized talk test provides an appropriate feedback, and then it may be harder for the user to convince him/herself that he/she is not working too hard.

Hyperventilation may enable the user to have better and smoother talk performance. Therefore, in one embodiment, the computerized talk test monitors the user's breathing rate in order to identify hyperventilation that may affect the results of the talk test. When hyperventilation is identified, one or more of the following may be performed: (i) providing a message asking the user to stop the hyperventilation, (ii) disregarding or skipping the upcoming talk test, (iii) compensating for the hyperventilation by adjusting the length of time the user should talk, such as increasing the length of time, (iv) adjusting the analysis to take into account the hyperventilation.

Some users may "prepare" themselves for the talk test by hyperventilation. Therefore, in one embodiment, the computerized talk test device runs the talk tests at varying or unexpected times. In one embodiment, the device monitors the user's breathing sounds, thereby identifying hyperventilation, and may optionally compensate for the hyperventilation or adjust the test results by repeating a test, extending a test, shortening a test, adjusting and/or changing the auditory signal, and/or altering the voice analysis algorithm.

Examples of healthy users of the computerized talk test device include, but are not limited to, one or more of the following: novice trainees, soldiers undergoing basic training, soldiers recuperating from injury, athletes going back to track, athletes resuming activity, athletes regaining former level of endurance, pregnant women, testers of athletic equipment/sports gear, and/or health club members.

Examples of unhealthy users of the computerized talk test device include, but are not limited to, cardiac patients and/or diabetics.

The theoretical target heart rate training zones may be inaccurate for patients prescribed certain medicines. For example, some cardiac patients, such as patients on Beta blockers or other medications, are unable to attain the target heart rate estimated by prediction formulas, such as the Karvonen method, to meet their training or rehabilitation program goals. These populations need to set their target heart rates for effective and safe exercise, especially when considering the safety boundaries around their appropriate target heart rate.

In one embodiment, the device executes a talk test, optionally with combined RPE indications, for determining the current pulse rate appropriate for the patient. For example, when considering the risks of exceeding the anaerobic threshold in cardiac patients, such as ischemia, it may be reasonable to execute quite frequent talk tests.

The target heart rates for patients who are recovering from heart disease depend to a large extent on various recovery conditions and/or physical strengths. The rehabilitation training frequencies should take into account the patients' specific condition. Using the computerized talk test, it is possible to adjust training parameters to fit these patients.

In one embodiment, a patient using a drug or medical device with cardiopulmonary effects, whether desired or side effects, may use the computerized talk test, optionally with RPE, for assessing his/her current target heart rate training zone, as it may be influenced by them. Therefore, the talk tests are performed from time to time. Running talk tests from time to time enables the device to ensure that the patient does not overtrain. The talk tests taken from time to time may vary in their frequency, duration, auditory signals, and/or any other characteristics that may take into account the patient's current situation and other available data, such as environmental conditions, patient's history, and/or known patterns.

In one embodiment, a training program for diabetics is based on ventilatory threshold, because exceeding the ventilatory threshold may carry the implication of overtraining, especially in diabetics with altered sensorium, and/or as exercising intensity increases, carbohydrate use increases. Indeed, as the ventilatory threshold changes from time to time, fine tuning the current heart rate training zone may be of use in optimizing differential utilization of bodily energy stores.

In one example, for patients prone to hypoglycemia, the computerized talk test may be used as a safety measure not to exceed the ventilatory threshold in order to avoid exhausting available sugar and carbohydrate stores. In another embodiment, for patients suffering from a decrease in insulin sensitivity and hyperglycaemia, the computerized talk test may be used to base a form of interval training on the ventilatory threshold, so that the routine exercise regimen will be made to utilize as much excess sugar and carbohydrates as bodily stores offer.

FIG. 11A, FIG. 11B, and FIG. 11C illustrate some non-limiting uses for some of the disclosed embodiments, but it is to be understood that none of the embodiments is limited to one or more of these benefits and/or uses. FIG. 9 illustrates some of the benefits of some of the disclosed embodiments, but it is to be understood that none of the embodiments is limited to, or must contain, one or more of these benefits.

In-the-Ear Device

In one embodiment, an in-the-ear computerized talk test device includes: a speaker for playing an auditory signal to be repeated by the user; a microphone for recording the user's voice while repeating the auditory signal; and a processor for identifying involuntary interruptions. Optionally, the processor receives RPE indications from the user; optionally, the RPE indications are entered through a mechanical user interface or using speech recognition. Optionally, the in-the-ear computerized talk test device communicates with a pulse watch (or other pulse measuring device), and optionally sets the heart rate training zone on the pulse watch.

In one embodiment, the elements of the in-the-ear device resemble the elements of talk-through-the-ear communication devices used for security applications. In one embodiment, the in-the-ear device includes a terminal located in one of the user's ears. Optionally, in order to extract the user's voice while playing sounds, the sounds played are deducted from the signals measured by the microphone.

A computerized talk test device may be used by a group of users. In one embodiment, each user in the group wears an in-the-ear microphone, preventing vocal interferences between the users. The auditory signal may be provided from one source to all of the users (for example by a loudspeaker, a trainer, or one of the users), or provided to each user separately using the in-the-ear device (wherein each user may receive a different auditory signal). FIG. 10A illustrates one non-limiting example of an in-the-ear device.

Computerized Talk Test Device Having a Throat Microphone

In one embodiment, a wearable computerized talk test device includes: a conduction microphone to record the user's voice while repeating an auditory signal; a processor for identifying involuntary interruptions; optional interface to a pulse watch; and a speaker, an earphone, or an earplug for playing an auditory signal to be repeated by the user. Examples of conduction microphones, which may be used by the disclosed embodiments to record the user's voice while repeating an auditory signal in a noisy environment, include, but are not limited to, a throat microphone, an ear bone conduction microphone, and a tooth bone conduction microphone such as described in U.S. Pat. No. 7,486,798, incorporated herein by reference.

Computerized talk tests may be performed, optionally simultaneously, by a group of users wearing conduction microphones, such as throat microphones or bone conduction microphones, preventing vocal interferences between the users. The auditory signal may be provided from one source to all of the users (for example by a loudspeaker, a trainer, or one of the users), or provided to each user separately (wherein each user may receive a different auditory signal). FIG. 10B illustrates one non-limiting example of a device including a throat microphone.

Ventilatory Threshold Software for a Communication Device

In one embodiment, the computerized talk test is performed using a communication device, such as a cellular phone. One embodiment of a computerized talk test using a communication device comprises the following steps: optionally, the user downloads a voice analysis software to his/her cellular phone; while training, the cellular phone records the user's voice; optionally, the user enters RPE indications, using the cellular phone's keypad or using speech recognition; when reaching the ventilatory threshold or an RPE threshold, the cellular phone signals the user to measure his/her pulse rate and/or to read a pulse meter.

Figure 7A:
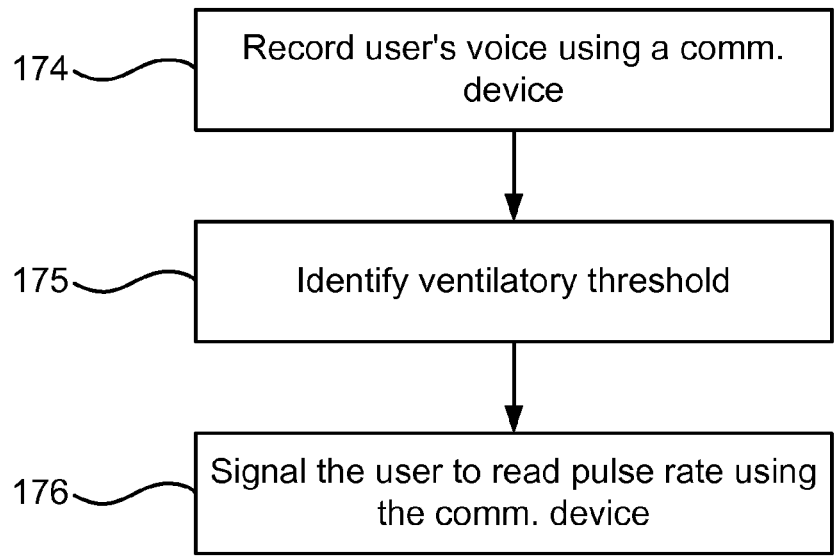
FIG. 7A and FIG. 7B illustrate embodiments of methods for performing computerized talk tests using a communication device.

FIG. 7A illustrates one embodiment of a method for performing a computerized talk test using a communication device, including the following steps. In step 174, recording a user's voice while training, using the communication device. In step 175, analyzing the recordings to identify when the user reaches the ventilatory threshold. And in step 176, using the communication device to instruct the user to read his/her pulse rate.

Another embodiment of a computerized talk test using a communication device comprises the following steps: (i) The user calls a talk test service using a communication device, such as, but not limited to, a cellular phone, a landline telephone, or a Voice-Over-Internet-Protocol device. (ii) The user performs a talk test; optionally, the talk test service determines when the user will perform the talk test; optionally, the talk test service provides an auditory signal and the user accompanies or repeats the auditory signal. (iii) The communication device transmits the user's voice to the talk test service for analysis of the user's voice. (iv) Optionally, the user enters RPE indications, using the interface of the communication device or using speech recognition. And (v) When reaching the ventilatory threshold or the RPE threshold, the communication device signals the user to measure pulse rate, and/or read a pulse meter; the signal is optionally a vocal, visual, and/or physical indication. Alternatively, the communication device communicates with the pulse meter. For example, a cellular phone may communicate with a pulse watch, optionally using the phone's short range communication means.

Optionally, the communication device communicates with a pulse rate sensor. Optionally, the communication device reads the pulse rate sensor and transmits the readings to the talk test service, or utilizes the readings to analyze the measurements.

Figure 7B:
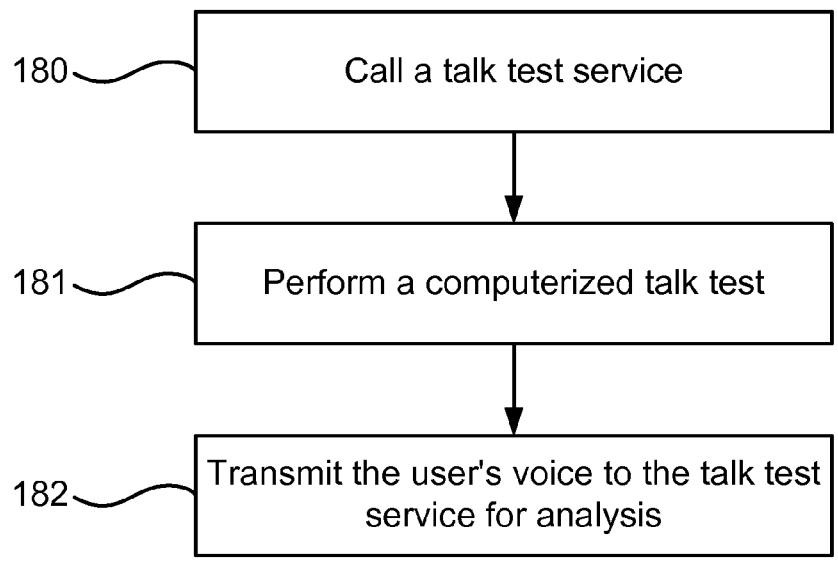

FIG. 7B illustrates one embodiment of a method for performing a computerized talk test using a communication device, including the following steps. In step 180, calling a talk test service using a communication device. In step 181, performing a computerized talk test. And in step 182, transmitting the user's voice to the talk test service for analysis. FIG. 10C illustrates one non-limiting example of a device based on a cellular phone.

Automatic Setting of the Target Heart Rate in a Pulse Meter

In one embodiment, a computerized talk test device is coupled to a pulse meter. After determining the ventilatory threshold or current heart rate training zone, the corresponding pulse rate is set as the target heart rate in the pulse meter or pulse tracking device.

In some cases, the exact target heart rate is a function of the current health, psychological state, and fitness of the user, and because they may change, sometimes even on a daily basis, the target heart rate may also change, even on a daily basis. Therefore, some of the disclosed embodiments are useful for a daily personalized fitness program based on the fine-tuned target heart rate. The current heart rate training zone may be fine-tuned before or during an extensive effort.

In one embodiment, the computerized talk test device is integrated with a pulse meter. Optionally, the current target heart rate training zone is determined automatically by the device based on one or more of the following: (i) the computerized talk test results; (ii) RPE indications; (iii) other relevant measurements of the user and/or the environment, such as body temperature, environment temperature, humidity level, hour, or other measurements; (iv) other inputs from the user, such as physical state, mental state, motivation level, use of medical devices, use of caffeine, use of narcotics, use of other drugs, or use of any material that may influence the current target heart rate training zone.

Figure 4:
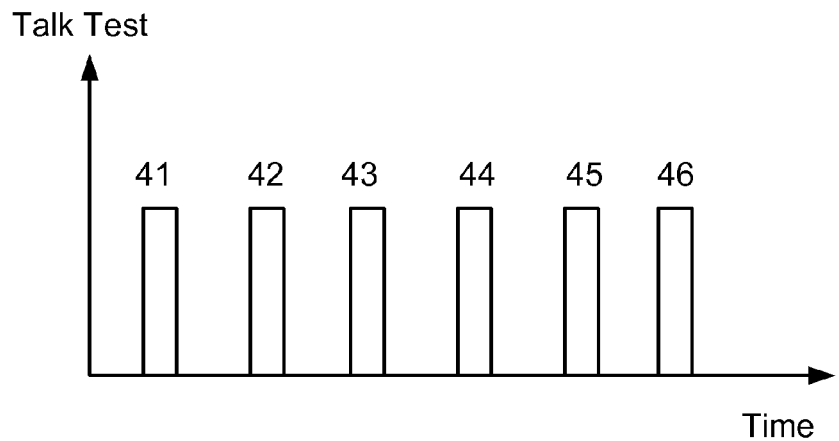
FIG. 4, FIG. 5A, and FIG. 5B illustrate modified talk tests.
Figure 5A:
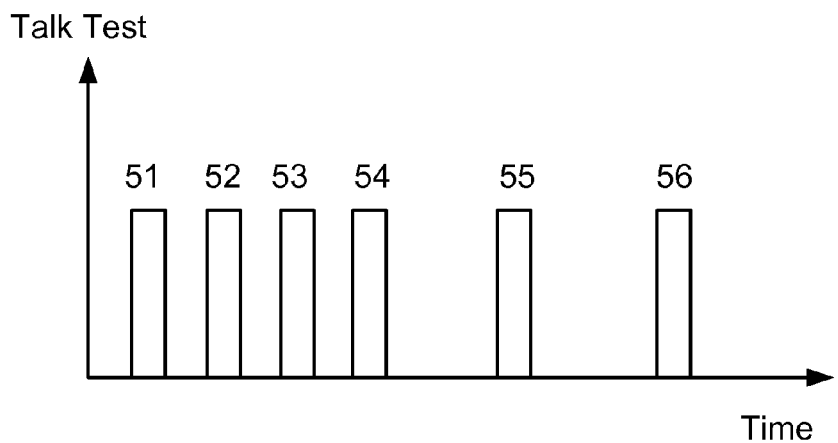
Figure 5B:
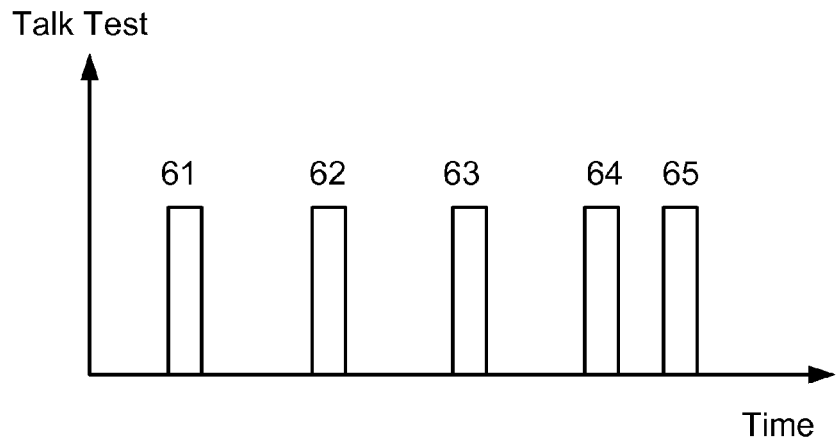

In one embodiment, a pregnant woman takes a computerized talk test, optionally combined with RPE indications to ensure she does not overtrain. FIG. 4 illustrates a modified talk test for pregnant women which includes taking talk test samples (41-46) throughout the exercise, and thereby ensuring no overtraining. FIG. 5A illustrates another modified talk test, which may be appropriate for pregnant women but also for many more types of users. The illustrated test includes a series of frequent talk tests (51-54) accompanied by less frequent talk tests (55, 56) throughout the exercise program. FIG. 5B illustrates a test including a series of less frequent talk tests (61-63) accompanied by frequent talk tests (64, 65).

Training Zones

In one embodiment, the heart rate training zone of a training program to be performed is set to be below, within, or above the current heart rate training zone estimated by the computerized talk test. In one embodiment, the current heart rate training zone is set to be below, within, or above the current estimated ventilatory threshold or the estimated ventilatory threshold. The estimated ventilatory threshold may be derived from any appropriate formula or obtained from any appropriate source. In one example, the talk test results in a pulse rate of approximately 130 bpm. A sub-ventilatory threshold training may be approximately around 110 bpm; a ventilatory threshold training may be approximately in the range of 120-140 bpm; and a supra-ventilatory threshold training may be approximately in the range of 140-160 bpm. In one embodiment, the current heart rate training zone estimated by the computerized talk test is set to be within a predefined range from the estimated target heart rate.

Optionally, the current heart rate training zone is set to be below, within, or above the current heart rate training zone estimated by the computerized talk test.

Optionally, the current heart rate training zone estimated by the computerized talk test is set to be below, within, or above the estimated target heart rate.

Optionally, the current heart rate training zone estimated by the computerized talk test is set to be within a predefined range from the estimated target heart rate.

In one embodiment, a user interface with an overall scale is provided to the user based on the average of the user's performance and the determined heart rate training zones. By selecting a particular day's workout, the user may access information regarding specific workouts, optionally on specific machines or regarding specific exercises. The exercise-specific information may show the target heart rate zone, the measured pulse rate, and other available measured or estimated performances.

In one embodiment, inspiring musical themes may inspire a user to persevere in the effort, maintaining or increasing pace as the user approximately approaches the ventilatory threshold or begins experiencing it. Examples of inspiring themes include a rhythmic track, a movie theme, or an instrumental piece noted for tempo.

The disclosed embodiments may be combined with devices and methods such as those disclosed in US patent application number 20060169125, entitled: "Musical pacemaker for physical workout", or US patent application number 20070060446, entitled: "Sound-output-control device, sound-output-control method, and sound-output-control program", both incorporated herein by reference in their entirety for all that they teach.

Speech Recognition

In one embodiment, an optional speech recognition feature is utilized for one or more of the following: (i) to initialize the device; (ii) to automatically load the appropriate user settings, history, and/or data; (iii) as a non-tactile method of controlling the input devices and or the progression of the test; and/or (iv) for acquiring the RPE indications. Optionally, the speech recognition is limited to a predefined set of words. Optionally, the speech recognition "learns" the user, and/or learns specific words pronounced by the user.

It is to be noted that the terms "anaerobic threshold" and "ventilatory threshold" may be used interchangeably for most of the disclosed embodiments and the inventors have no intention to limit the scope of embodiments to one of these terms.

In one embodiment, the computerized talk test device utilizes a regular microphone. The sound processing algorithm may utilize noise canceling and/or noise filtering techniques. Optionally, the device learns the characteristics of the user's voice for improving the performance of the sound processing algorithm.

Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination.

The embodiments are not limited in their applications to the details of the order or sequence of steps of operation of methods, or to details of implementation of devices, set in the description, drawings, or examples. Moreover, the individual blocks illustrated in the block diagrams herein may be functional in nature and do not necessarily correspond to discrete hardware elements.

While the methods disclosed herein have been described and shown with reference to particular steps performed in a particular order, it will be understood that these steps may be combined, sub-divided, or reordered to form an equivalent method without departing from the teachings of the embodiments. Accordingly, unless specifically indicated herein, the order and grouping of the steps is not a limitation of the embodiments.

While the embodiments have been described in conjunction with specific examples thereof, it is to be understood that they have been presented by way of example, and not limitation. Moreover, it is evident that many alternatives, modifications and variations will be apparent to those skilled in the art. It is to be understood that other embodiments may be utilized and structural changes may be made without departing from the scope of the embodiments. Accordingly, it is intended to embrace all such alternatives, modifications and variations that fall within the spirit and scope of the appended claims and their equivalents. In the claims, means-plus-function clauses are intended to cover the structures described herein as performing the recited function and not only structural equivalents, but also equivalent structures.

What is claimed is:

1. A device comprising:
   a memory configured to store a recording of a user talk;
   a processor configured to: receive an estimated heart rate training zone of the user, receive measured pulse of the user, run a non-empty series of less frequent computerized talk tests, which analyze the recording for involuntary interruptions in the user talk, when the measured pulse is below the estimated heart rate training zone; and
   the processor is further configured to: run a non-empty series of frequent computerized talk tests, which analyze the recording for involuntary interruptions in the user talk, when the measured pulse is in the estimated heart rate training zone.

2. The device of claim 1, wherein the device is configured to receive the estimated heart rate training zone by a voice indication through a microphone.

3. The device of claim 1, wherein the device is further coupled to an input component, and the device receives the estimated heart rate training zone through the input component.

4. The device of claim 1, wherein the device is further configured to perform at least one of the computerized talk tests while the user essentially sustains a fixed level of effort.

5. The device of claim 4, wherein the device is further configured to communicate with a controllable exercise device, whereby coordination between the device and the controllable exercise device enables the performance of the computerized talk test while the user essentially sustains the fixed level of effort.

6. The device of claim 4, wherein the device is further configured to communicate with an effort-assessment-device, whereby coordination between the device and the effort-assessment-device enables the performance of the computerized talk test while the user essentially sustains the fixed level of effort.

7. The device of claim 1, further comprising a conduction microphone for taking the recording of the user talk in a noisy environment.

8. The device of claim 1, wherein the device is an in-the-ear device.

9. The device of claim 1, wherein the device is a mobile phone.

10. The device of claim 1, further comprising a mobile phone configured to provide the user with the heart rate training zone that was determined based on the computerized talk tests.

11. A computer-implemented method comprising:
    storing, in a memory, a recording of a user talk;
    receiving, by a processor, an estimated heart rate training zone of the user, and measured pulse of the user;
    running, by the processor, a non-empty series of less frequent computerized talk tests, which analyze the recording for involuntary interruptions in the user talk, when the measured pulse is below the estimated heart rate training zone; and
    running, by the processor, a non-empty series of frequent computerized talk tests, which analyze the recording for involuntary interruptions in the user talk, when the measured pulse is in the estimated heart rate training zone.

12. The computer-implemented method of claim 11, further comprising receiving the estimated heart rate training zone by a voice indication through a microphone.

13. The computer-implemented method of claim 11, further comprising receiving the estimated heart rate training zone through an input component.

14. The computer-implemented method of claim 11, further comprising performing at least one of the computerized talk tests while the user essentially sustains a fixed level of effort.

15. The computer-implemented method of claim 14, further comprising communicating with a controllable exercise device for performing the computerized talk test while the user essentially sustains the fixed level of effort.

16. The computer-implemented method of claim 14, further comprising communicating with an effort-assessment-device for performing the computerized talk test while the user essentially sustains the fixed level of effort.

17. The computer-implemented method of claim 11, further comprising a conduction microphone for taking the recording of the user talk in a noisy environment.

18. The computer-implemented method of claim 11, wherein the method is implemented by a mobile phone.

* * * * *